United States Patent [19]
Nagy et al.

[11] Patent Number: 5,141,617
[45] Date of Patent: Aug. 25, 1992

[54] ELECTROCHEMICAL CELL

[75] Inventors: Zoltan Nagy, Woodridge; Robert M. Yonco, LaGrange; Hoydoo You, Naperville; Carlos A. Melendres, Lemont, all of Ill.

[73] Assignee: The United States of America as represented by the United States Department of Energy, Washington, D.C.

[21] Appl. No.: 689,426

[22] Filed: Apr. 23, 1991

[51] Int. Cl.⁵ .................. C25B 9/00; C25B 15/00; C25C 7/00; C25C 7/04
[52] U.S. Cl. .................. 204/231; 204/252; 204/266
[58] Field of Search .............. 204/252–258, 204/263–266, 282–283, 231, 435

[56] References Cited

U.S. PATENT DOCUMENTS

| | | | |
|---|---|---|---|
| 3,374,161 | 3/1968 | Zatz | 204/266 X |
| 3,676,220 | 7/1972 | Ward, III | 204/266 X |
| 4,163,698 | 8/1979 | Kuo et al. | 204/435 X |
| 4,310,400 | 1/1982 | Mark, Jr. et al. | 204/435 X |
| 4,500,402 | 2/1985 | Miles et al. | 204/252 X |
| 4,623,440 | 11/1986 | Cairns | 204/252 X |

OTHER PUBLICATIONS

Robinson, "X-Ray Techniques", *Spectrochemistry Theory and Practice*, pp. 9 and 22-25, (Plenum Press, 1988).
Bosio et al., "Exafs as a Probe of the Passive Film Structure", Elsevier Science Pub. B.V., Amsterdam, (1983).
Bosio et al., "ReflEXAFS Studies of Protective Oxide Formation on Metal Surfaces", Proc. of the 3rd Intntl EXAFS Conf. (1984).
Curtiss et al., "In-Situ Electromagnetic Techniques", Corrosion Research and Progress Symp., (NACE, Apr. 23-24, 1990).
Nagy et al., "Cell Design for In-Situ X-Ray Scattering Study of Electrodes in Transmission Geometry", *Electrochemica Acta*, vol. 36, No. 1, pp. 209-212, (1991).

*Primary Examiner*—Donald R. Valentine
*Attorney, Agent, or Firm*—Hugh W. Glenn; Robert J. Fisher; William R. Moser

[57] ABSTRACT

An electrochemical cell has a layer-type or sandwich configuration with a Teflon center section that houses working, reference and counter electrodes and defines a relatively narrow electrolyte cavity. The center section is surrounded on both sides with thin Teflon membranes. The membranes are pressed in place by a pair of Teflon inner frames which are in turn supported by a pair of outer metal frames. The pair of inner and outer frames are provided with corresponding, appropriately shaped slits that are in plane generally transverse to the plane of the working electrode and permit X-ray beams to enter and exit the cell through the Teflon membranes that cover the slits so that the interface between the working electrode and the electrolyte within the cell may be analyzed by transmission geometry. In one embodiment, the center section consists of two parts, one on top of the other. Alternatively, the center section of the electrochemical cell may consist of two intersliding pieces or may be made of a single piece of Teflon sheet material. The electrolyte cavity is shaped so that the electrochemical cell can be rotated 90° in either direction while maintaining the working and counter electrodes submerged in the electrolyte.

20 Claims, 2 Drawing Sheets

ELECTROCHEMICAL CELL

CONTRACTUAL ORIGIN OF THE INVENTION

The United States government has rights in this invention pursuant to contract No. W-31-109-ENG-38 between the United States Department of Energy and The University of Chicago representing Argonne National Laboratory.

BACKGROUND OF THE INVENTION

1. Field of the Invention

The present invention relates generally to an electrochemical cell and more particularly, to a new and improved electrochemical cell that is adapted for in situ scattering studies of the interface between a working electrode of the cell and electrolyte contained in the cell based on transmission geometry.

2. Background of the Invention

In an electrochemical cell, a solid working electrode is submerged in a liquid electrolyte. X ray techniques have been increasingly used in order to investigate in situ the interface between the working electrode and the liquid electrolyte. For the most part, extended X-ray absorption fine structure (EXAFS) techniques have been used to probe for chemical or short-range structural information as to the interface between the electrode and the liquid electrolyte. Typically, the EXAFS measurements are accomplished in a reflection geometry.

In such a reflection geometry, a membrane has to be pulled taut over the working electrode surface so that the solution layer through which the X rays must travel is minimized. An incoming X-ray beam is transmitted through the membrane and the electrolyte onto the working electrode. A detector receives the reflected beam and determinations can be made about the surface from which the X-ray is reflected by scattering techniques. When such a reflection geometry is used, the X-rays are reflected not only from the electrochemical interface between the working electrode and the electrolyte, but also from the air/membrane and membrane/solution interfaces through which the incoming X-ray beams must pass. As a result, the reflective data obtained when a reflection geometry is used requires deconvolution or subtraction of the interference that occurs from the air/membrane and membrane/solution interfaces. In addition, the nature of those additional interfaces also may vary making it even more difficult to correctly interpret the data received.

Other factors also tend to make it more difficult to correctly interpret data obtained when using reflection geometry. The current distribution over the working electrode surface in an electrochemical cell may be nonuniform due to the geometric arrangement of the electrodes and the large ohmic resistance in the electrolyte gap. The electrolyte gap may be expanded by inflating the membrane or withdrawing the electrode assembly during electrochemical manipulations. Yet, the electrolyte gap is constricted during the X-ray measurements so that meaningful data may not be obtained. In addition, absorption corrections must be made when using reflection geometry due to the change at small angles in the path length over which X ray beams travel. Moreover, there is a tendency for the diffuse background to rise rapidly at small scattering angles in the reflection geometry. Therefore, the total signal is reduced by absorption but the diffuse background from the air/membrane and the membrane/solution interfaces are hardly attenuated resulting in a low signal to background ratio at small angles. As a result, it would be preferable to use transmission geometry when analyzing the interface between an electrode and electrolyte in an electrochemical cell. In the case of a transmission geometry, the X-ray beam could be transmitted through membranes disposed transversely to and on opposite sides of the electrode. As a result, the X-rays reflect to the detector only from the electrochemical interface and the reflectivity data can be interpreted directly instead of requiring the processing needed in the case of reflection geometry. Moreover, little absorption correction is required in using transmission geometry because the path length of the X-rays is nearly constant over the angular range of interest. In addition, the diffuse background is attenuated as much as the signal in the transmission geometry such that the signal to background ratio remains constant over the full angular range of interest.

Consequently, it would be advantageous to utilize transmission geometry instead of reflection geometry in studying the electrode/electrolyte interface in an electrochemical cell. However, a suitable electrochemical cell has not heretofore been available that is constructed such that transmission geometry can be readily utilized.

SUMMARY OF THE INVENTION

Accordingly, it is an object of the present invention to provide a new and improved electrochemical cell that is adapted to utilize transmission geometry in studying an electrode/electrolyte interface with X-ray scattering techniques.

Another object of the present invention is to provide a new and improved electrochemical cell that is relatively narrow and includes windows covered by a thin TEFLON membrane on opposite sides of the working electrode and disposed in planes generally perpendicular to the plane of the working electrode so that X-ray beams can be transmitted through one of the windows, impinge on the electrode/electrolyte interface and reflect through the opposite window.

Yet another object of the present invention is to provide a new and improved electrochemical cell having a layer-type or sandwich configuration in which a TEFLON center section housing the electrodes and defining an electrolyte cavity is made of intersliding pieces or a single piece of TEFLON sheet material.

A further object of the present invention is to provide a new and improved electrochemical cell having a layer-type or sandwich configuration in which a TEFLON center section houses the electrodes and shapes the electrolyte cavity and is surrounded on both sides with a TEFLON membrane.

Still another object of the present invention is to provide a new and improved electrochemical cell that enables the studying of the electrode/electrolyte interface with transmission geometry but at the same time permits the rotation of the cell by 90° in either direction while maintaining a gas space above the electrolyte and maintaining the working and counter electrodes fully submerged in the electrolyte.

In accordance with these and many other objects of the present invention, an electrochemical cell embodying the present invention has a layer-type or sandwich configuration with a TEFLON center section that houses the electrodes and defines a relatively narrow electrolyte cavity. The center section is surrounded on both sides with thin TEFLON membranes. The membranes are pressed in place by a pair of TEFLON inner frames which are in turn supported by a pair of outer metal frames. The pair of inner and outer frames are provided with corresponding, appropriately shaped slits that permit X-ray beams to enter and exit the cell through the TEFLON membranes that cover the center section. The provision of such slits and windows on opposite sides of the working electrode and in planes that are perpendicular to the plane of the working electrode permits the use of transmission geometry in studying the interface between the working electrode and the electrolyte within the cell. The cell assembly is held together by bolts that compress the inner frames and the center section to provide a solution-tight seal around the edges.

In one embodiment of the electrochemical cell of the present invention, the center section consists of two parts. One of the parts is a bottom support that holds a metal coated substrate forming the working electrode. The other part is a top cover piece which defines the electrolyte cavity and contains the counter and reference electrodes and the leads for the working electrode. Such a design also permits the use of working electrodes made of a solid metal slab so that a direct electrical contact can be made to the working electrode at the bottom of the electrochemical cell.

Alternatively, the center section of the electrochemical cell of the present invention may consist of two intersliding pieces. A better seal can be attained with this arrangement. Leakage of liquid between the two pieces can be avoided by a compressive seal at the top of the center piece using frame mounted set screws. On the other hand, an even better seal may be provided when the center section in made of a single piece of TEFLON sheet material.

BRIEF DESCRIPTION OF THE DRAWINGS

Many other objects and advantages of the present invention will become apparent from considering the following detailed description of the embodiments of the invention illustrated in the drawings, wherein.

EXPLANATION OF REFLECTION AND TRANSMISSION GEOMETRY

Figure 1:
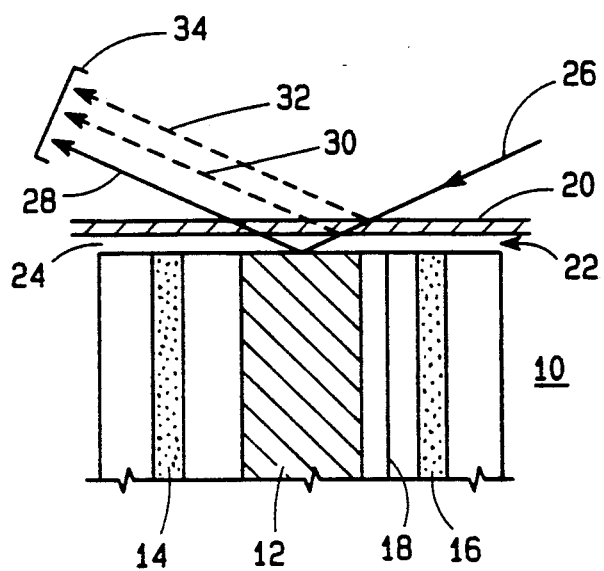
FIG. 1 is a schematic cross-sectional view of a portion of an electrochemical cell that illustrates how reflection geometry may be used in order to obtain information with respect to the interface between an electrolyte and a working electrode.
Figure 2:
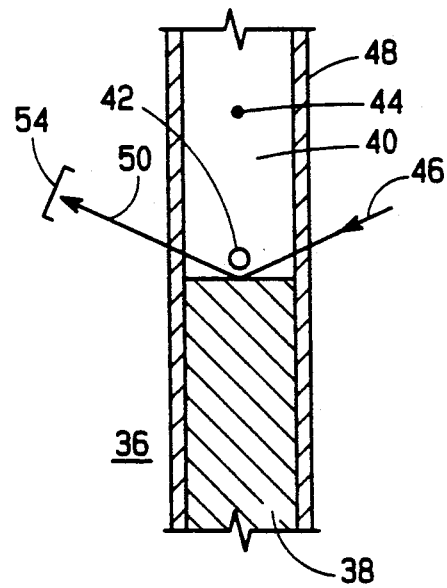
FIG. 2 is a schematic cross-sectional view of a portion of another type of electrochemical cell that illustrates how transmission geometry may be used to obtain information with respect to the interface between an electrolyte and a working electrode.

FIGS. 1-2 illustrate how reflection and transmission geometries are used in analyzing a working electrode of an electrochemical cell. In particular, FIGS. 1-2 illustrate the advantages attained by using transmission geometry by disclosing schematically the difference between using reflection geometry to analyze a working electrode of an electrochemical cell (FIG. 1) and using transmission geometry to analyze such an electrode (FIG. 2).

Referring now more specifically to FIG. 1 of the drawings, therein is shown schematically a cross-section of a portion of an electrochemical cell 10. The electrochemical cell 10 includes a working electrode 12, counter electrodes 14 and 16 and a reference electrode 18. A membrane 20 is positioned above and parallel to the working electrode 12 so as to form a electrolyte gap 22 that is filled with an electrolyte 24. In order to obtain information concerning the interface between the working electrode 12 and the electrolyte 24 by means of reflection geometry, an X ray beam 26 is projected at an incoming angle with respect to the surfaces of the membrane 20 and the working electrode 12. As seen in FIG. 1, the X-ray beam 26 passes through the membrane 20 and impinges on the working electrode 12. As a result, reflective beams 28, 30 and 32 are reflected respectively from the interface between the electrolyte 24 and the working electrode 12, the interface between the membrane 20 and the electrolyte 24 and the interface between the membrane 20 and the air above the membrane 20. The reflective beams 28, 30, and 32 are received by a detector 34 and can be analyzed to determine information about the interface between the working electrode 12 and the electrolyte 24.

As can be appreciated from FIG. 1, the fact that the X-ray beam 26 is reflected from a multiplicity of interfaces results in a plurality of reflective beams 28, 30 and 32. The multiplicity of reflective beams 28, 30 and 32 complicates the analysis of the information concerning the interface between the working electrode 12 and the electrolyte 24. In addition, the changes in the path length over which the X-ray beams 26 and 28 travel due to small angular changes in their paths tends to require the making of absorption corrections and tends to result in signals with low signal to background ratios.

On the other hand, the use of transmission geometry as illustrated in FIG. 2 of the drawings enables the reflective data to be interpreted directly without the necessity of correcting the data for additional reflective beams. More specifically and with reference to FIG. 2 of the drawings, an alternate electrochemical cell 36 is schematically disclosed therein that enables the use of transmission geometry to obtain information concerning the interface between a working electrode 38 and an electrolyte 40 in which the working electrode 38 is submerged. The electrochemical cell 36 includes the working electrode 38, a reference electrode 42 and a counter electrode 44. In order to determine information concerning the interface between the working electrode 38 and the electrolyte 40 by means of transmission geometry, an X-ray beam 46 is projected onto the surface of the working electrode 38 through a membrane 48 that lies in a plane that is generally perpendicular or transverse to the plane of the working electrode 38. The X-ray beam 46 impinges on the working electrode 38 at an angle such that a reflective beam 50 is reflected from the interface between the electrolyte 40 and the working electrode 38. The reflective beam 50 travels through another membrane 52 that is positioned in a plane that is parallel to the plane of the membrane 48 and generally perpendicular or transverse to the plane of the working electrode 38 on an opposite side of the working electrode 38 from the membrane 48. The reflective X-ray beam 50 is received by a detector 54 and can be analyzed to determine information about the interface between the working electrode 38 and the electrolyte 40. In view of the fact that only a single reflective X-ray beam 50 is reflected and received by the detector 54, information concerning the interface between the working electrode 38 and the electrolyte 40 can be readily analyzed. Moreover, the path length over which the X-ray beam 46 and the reflective beam 50 travel are essentially constant over the angular range of interest thereby eliminating the need of absorption correction and the signal to background ratio is significantly greater than in the case of signals received when a reflection geometry illustrated in FIG. 1 is used.

DETAILED DESCRIPTION OF THE PREFERRED EMBODIMENTS

Figure 3:
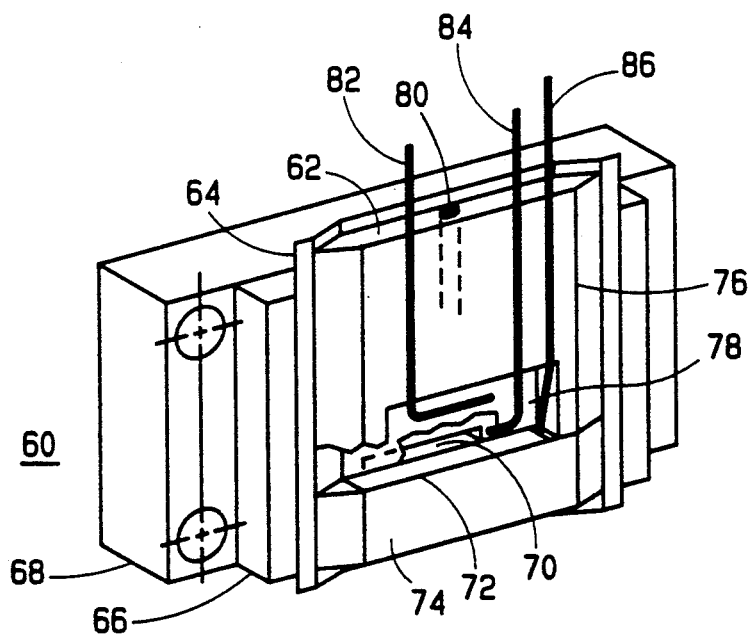
FIG. 3 is a schematic, perspective view of a center section and one of a pair of framing portions of an electrochemical cell embodying the present invention.

Referring now more specifically to FIG. 3 of the drawings, therein is disclosed an electrochemical cell generally designated by the reference numeral 60 and embodying the present invention. Only one half of the electrochemical cell 60 is illustrated in FIG. 3, the other half being a mirror image of the portion disclosed in FIG. 3. The electrochemical cell 60 has a layer-type or sandwich configuration and includes a center section 62 surrounded by thin TEFLON membranes, one of which is illustrated as membrane 64. The membranes, such as the membrane 64, are pressed in place by a pair of TEFLON inner frames (an inner frame 66 being shown in FIG. 3) which are supported by a pair of outer metal frames (an outer frame 68 being shown in FIG. 3). The inner frames 66 and the outer frames 68 have aligned windows or slits 70 that permit X-ray beams to penetrate and exit the electrochemical cell 60 through the TEFLON membranes 64. As a result, transmission geometry may be utilized in studying a working electrode 72 supported in the center section 62.

More specifically, the center section 62 of the electrochemical cell 60 includes the working electrode 72 that may be in the form of a metal coated substrate mounted on a working electrode support 74. The working electrode support 74 may be made of a TEFLON material, but alternatively, the working electrode 72 may be made of a solid metal slab such that an electrical connection can be made directly to the bottom of the working electrode support 74. The working electrode support 74 with the working electrode 72 thereon forms one portion of the center section 62 while a cover piece 76 forms the other portion of the center section 62.

The cover 76 may be made of a TEFLON material and defines an electrolyte cavity 78 into which an electrolyte may be added through an inlet tube 80. The cover 76 also supports a counter electrode 82, a reference electrode 84 and a working electrode lead 86 that is coupled to the working electrode 72. As seen in FIG. 3, the ends of the counter electrode 82 and the reference electrode 84 as well as the working electrode 72 project into the electrolyte cavity 78 and are thereby submerged in the electrolyte contained in the electrolyte cavity 78. The components that form the electrochemical cell 60 including the cover 76, the inner frames 66 and the membranes 64 are held together by bolts (not shown) that extend between the outer frames 68 such that the inner frames 66 and the center section 62 are compressed together to form a solution-tight seal around the edges of the center section 62 and such that the membranes 64 are pressed into place between the inner frames 66. The outer frames 68 may be equipped with appropriate mounting fixtures (not shown) so that a four-circle X ray spectrometer may be attached to the electrochemical cell 60.

As previously indicated, the electrochemical cell 60 includes the aligned slits 70 in the outer frames 68 and the inner frames 66. The internal surface of slits 70 are covered by the membranes 64 and lie in a plane generally perpendicular to the plane of and on opposite sides of the working electrode 72 The configuration of the slits 70 and the membranes 64 relative to the working electrode 72 permits X-ray beams to be used in a transmission geometry to analyze the interface between the electrolyte in the electrolyte cavity 78 and the working electrode 72. In this regard, the X-ray beams may be projected through one of the slits 70 and the membrane 64 covering that slit 70 through the electrolyte and impinge on the working electrode 72. The resulting reflective beam then travels through the electrolyte and the opposite the membrane 64 and slit 70 so that it may be received and analyzed by a detector (not shown) associated with the electrochemical cell 60. The configuration of the electrochemical cell 60 enables the electrochemical cell 60 to be relatively narrow. In fact, the thickness of the electrochemical cell 60 is preferably selected to be equal to an absorption length of 1Å X-ray so as to optimize the thickness of the electrochemical cell 60 to the absorption length of X-rays used.

One of the difficulties with the design of the electrochemical cell 60 shown in FIG. 3 is that it is difficult to achieve a perfect seal and to avoid electrolyte leakage unless the mating surfaces of the inner frames 66 and the center section 62 are very precisely machined. In order to avoid the severe machining requirements needed for such an electrochemical cell, the inner frames and center sections of an electrochemical cell can be made from flat Teflon sheets. Such designs are disclosed in FIGS. 4-5 of the drawings.

Figure 4:
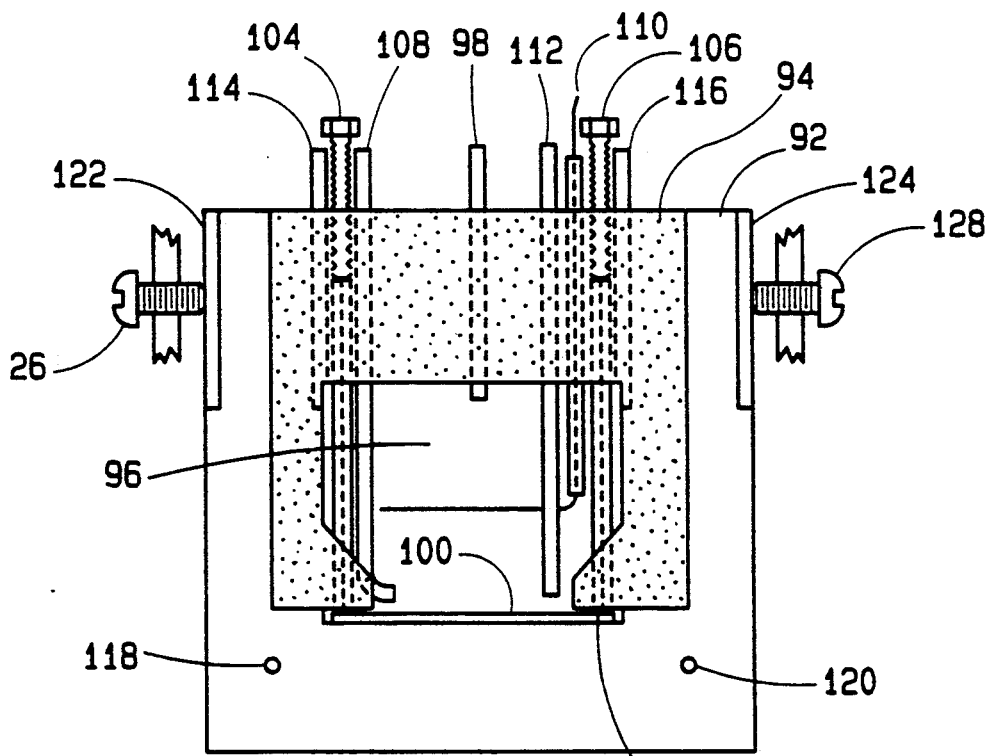
FIG. 4 is a cross-sectional view of an alternate center section for use in an electrochemical cell of the type illustrated in FIG. 3 and embodying the present invention.

With respect to the design disclosed in FIG. 4, a center section 90 of an electrochemical cell is schematically shown. The center section 90 may be used in an electrochemical cell having other components essentially the same as the electrochemical cell 60 disclosed in FIG. 3 of the drawings.

The center section 90 disclosed in FIG. 4 includes two intersliding pieces, namely an outer center section 92 and an inner center section 94. The inner center section 94 defines an electrolyte cavity 96 into which an electrolyte is added through an inlet tube 98. A working electrode 100 formed of metal or with metal foils 102 is positioned at the bottom of the electrolyte cavity 96. Working electrode leads 104 and 106 extend to the opposite ends of the working electrode 100 and are mounted in the inner center section 94. A reference electrode 108 and a counter electrode 110 also are mounted in the inner center section 94 and extend into the electrolyte cavity 96 so that the ends of the electrodes 108 and 110 are submerged in the electrolyte. In addition, a gas inlet 112 and vents 114 and 116 extend to the electrolyte cavity 96 through the inner center section 94.

The outer center section 92 is provided with positioning holes 118 and 120. In order to provide a compressive seal between the outer center section 92 and the inner center section 94 of the center section 90, metal inserts 122 and 124 are disposed on opposite sides of the outer center section 92 so that frame mounted set screws 126 and 128 may apply compressive forces to the outer center section 92.

As was the case with respect to the electrochemical cell 60, the use of the center section 90 permits the use of transmission geometry to obtain information as to the interface between the electrolyte contained in the electrolyte cavity 96 and the working electrode 100. This is because the outer and inner frames, such as the inner frames 66 and the outer frames 68 of the electrochemical cell 60, provide slits that lie in a plane generally perpendicular to and on opposite sides of the working electrode 100 and compress the membrane against the center section to form a water-tight seal. As a result, X-ray beams may be projected into the electrolyte cavity 96 and impinge on the surface of the working electrode 100 in a transmission geometry.

Even though the center section 90 disclosed in FIG. 4 provides a better sealing arrangement than the center section 62 used in the electrochemical cell 60 of FIG. 3, a still better seal can be attained if the center section of the electrochemical cell is made from a single piece of TEFLON sheet material. Such a single piece design is illustrated schematically in FIG. 5 in which a center section 140 is disclosed. The center section 140 consists of a single central portion 142 that provides a better seal for an electrolyte cavity 144 even though it is more difficult to construct than the previously discussed center sections 62 and 90.

The center section 140 has its electrolyte cavity 144 filled with an electrolyte through an inlet tube 146. A working electrode 148 which may be solid metal or a metal coated substrate is positioned at the bottom of the electrolyte cavity 144 with metal foils 150. Working electrode leads 152 and 154 extend through the bottom of the central portion 142 and coupled to the metal foils 150 at opposite ends of the working electrode 148. A reference electrode 156 and a counter electrode 158 also are mounted on the central portion 142, the ends of which extend into the electrolyte cavity 144 and are therefore submerged in the electrolyte as is the working electrode 148. The electrolyte cavity 144 additionally is provided with a gas inlet 160, and a pair of air vents 162 and 164 on either side of the electrolyte cavity 144. A purge hole 166 extends to the space below the working electrode 148 so that the space may be purged or filled. The central portion 142 also is provided with a pair of positioning holes 168 and 170.

As was the case with respect to the center sections 62 and 90, the center section 140 enables transmission geometry to be used in studying the interface between the electrolyte in the electrolyte cavity 144 and the working electrode 148. This is because the outer and inner frames, such as the inner frames 66 and the outer frames 68 of the electrochemical cell 60, provide slits that lie in a plane generally perpendicular to and on opposite sides of the working electrode 148 and compress the membrane against the center section to form a water-tight seal. As a result, X-ray beams may be projected into the electrolyte cavity 144 and impinge on the surface of the working electrode 148 in a transmission geometry.

Moreover, all three center sections 62, 90 and 140 are designed with electrolyte cavities 78, 96 and 144 shaped such that the cell may be rotated 90° in either direction and still a gas space is provided above the electrolyte and the working electrodes 72, 100 and 148 and the counter electrodes 82, 110 and 158, respectively, will still be fully submerged in the electrolyte. In this regard and as specifically illustrated with respect to the center sections 90 and 140 two vent holes (the vents 114 and 116 in the case of the center section 90 and the vents 162 and 164 in the case of center section 140) are positioned at opposite upper corners of the electrolyte cavities 96 and 144 respectively.

The input/output connections for the center sections 62, 90 and 140, such as the inlet tubes 80, 98 and 146; the vents 114, 116, 162 and 164; the gas inlet 160 and the purge hole 166, can be made of a TEFLON tubing that is tightly disposed in holes in the TEFLON sheet from which the center sections 62, 90 and 140 are formed. In addition, the coupling of the working electrode lead 86 to the working electrode 72, the working electrode leads 104 and 106 to the working electrode 102 and the working electrode leads 152 and 154 to the working electrode 148 is accomplished by coupling the respective working electrode leads to opposite ends of the working electrodes 72, 102 or 148 using lead wires that are pressed to the metal foil that is in contact with the respective working electrodes 72, 102 or 148, such as the foil 102 or 150. Such lead wires are insulated from the electrolyte in the electrolyte cavities 78, 96 and 144 by tight-fitting Teflon tubing that also serve as a sealant. The lead wires associated with the working electrode leads 86, 104, 106, 152 and 154 and the foils 102 and 150 can be made of inert metals or of the same metal as the working electrodes 72, 100 and 148.

Figure 5:
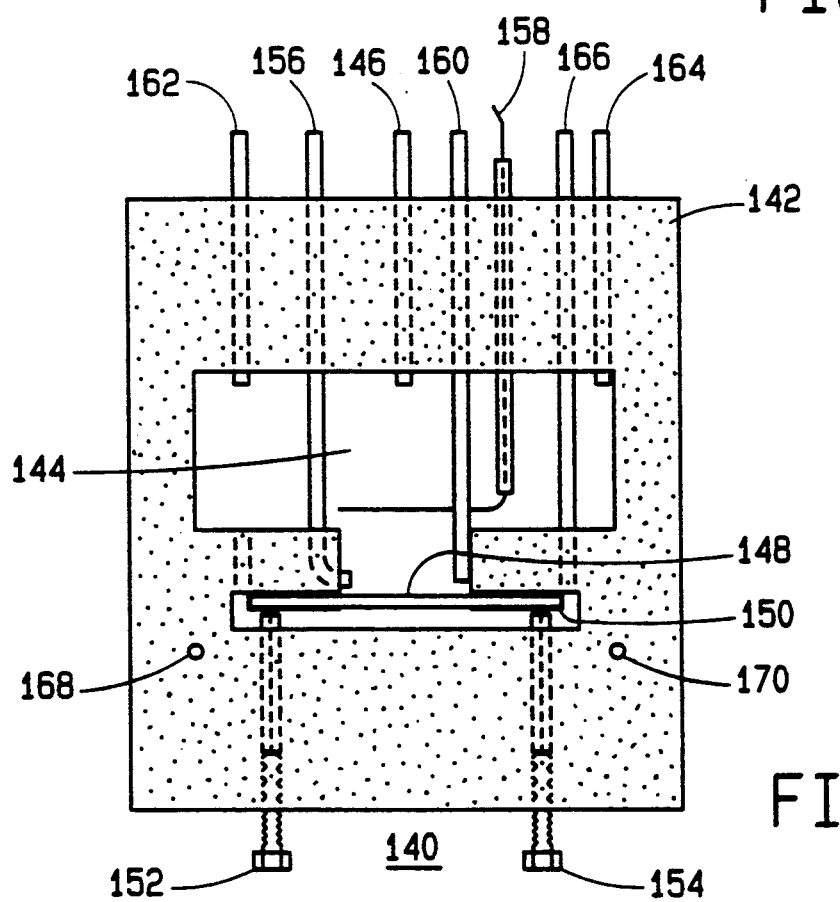
FIG. 5 is a cross-sectional view of another alternate center section for use in an electrochemical cell of the type illustrated in FIG. 3 and embodying the present invention.

As seen in FIGS. 3-5, the counter electrodes 82, 110 and 158 may be made of inert metal wire and traverse the full length of the respective working electrodes 72, 100 and 148 so as to provide a uniform current distribution. On the other hand, the reference electrodes 84, 108 and 156 are disposed close to their respective working electrodes 72, 100 and 148 to ensure a small uncompensated IR-drop in the electrolyte solution contained in the electrolyte cavities 78, 96 and 144. When internal reference electrodes 84, 108 and 156 are used, the reference electrodes 84, 108 and 156 may be made of chloride or oxide coated silver wire sheathed in TEFLON tubing except for a short distance at the working end thereof. Alternatively, an external reference electrode may be used with a small TEFLON tube serving as both a Luggin tip and solution bridge.

Although the invention has been described with cell components of TEFLON, it is to be understood that other polymeric plastic materials that are chemically compatible with the electrolyte solution also may be used. For example, MYLAR KAPTON KEL-F, polypropylene or TEFZEL may be used for the membrane and KEL-F or TEFZEL may be used for the frame, center section and tubing.

While the invention has been described wit reference to details of the illustrated embodiments, these details are not intended to limit the scope of the invention as defined in the appended claims.

The embodiment of the invention in which an exclusive property or privilege is claimed is defined as follows:

1. An electrochemical cell having an electrolyte cavity adapted to contain an electrolyte with at least a working electrode disposed therein and submerged in said electrolyte contained in said electrolyte cavity, said electrochemical cell comprising:

frame means;

a center means mounted within said frame means, said center means defining said electrolyte cavity in which said working electrode is mounted such that an interface is formed between said working electrode and said electrolyte;

membrane means disposed on opposite sides of said center means to provide a seal with said center means; and window means in said frame means over which said membrane means is disposed, said window means being in a plane that is generally transverse to the plane of the working electrode.

2. The electrochemical cell as set forth in claim 1 wherein said center means is formed from a polymeric plastic material.

3. The electrochemical cell as set forth in claim 1 wherein said center means includes a single piece of polymeric plastic material.

4. The electrochemical cell as set forth in claim 1 wherein said center means is formed from inner and outer intersliding pieces made of polymeric plastic material with said electrolyte cavity being formed in the inner one of said pieces and compressive means to apply a compressive force to maintain said inner and outer intersliding pieces together.

5. The electrochemical cell as set forth in claim 1 wherein said center means includes a bottom support means for said working electrode and a top cover piece which defines said electrolyte cavity.

6. The electrochemical cell as set forth in claim 1 wherein said frame means includes inner frame means and an outer frame means, said inner frame means and said outer frame means having aligned slits forming said window means.

7. The electrochemical cell as set forth in claim 6 wherein said inner frame means is made of polymeric plastic material and said outer frame means is made of metal.

8. The electrochemical cell as set forth in claim 6 including fastening means to compress said inner frame means against said center means so as to form a solution-tight seal around the edges of said center means.

9. The electrochemical cell as set forth in claim 1 including vent means at opposite ends of said electrolyte cavity, the shape of said electrolyte cavity and said vent means allowing said electrochemical cell to be rotated 90° while maintaining a gas space above said electrolyte and maintaining said working electrode submerged in said electrolyte.

10. An electrochemical cell having an electrolyte cavity adapted to contain an electrolyte with a working electrode, a reference electrode and a counter electrode disposed therein and submerged in said electrolyte contained in said electrolyte cavity, said electrochemical cell comprising:

outer frame means;

inner frame means;

a center means having said electrolyte cavity in which said working, reference and counter electrodes are mounted such that an interface is formed between at least said working electrode and said electrolyte;

membrane means disposed on opposite sides of said center means and between said inner frame means and said center means in order to provide a seal about said center means;

fastening means associated with said outer and inner frame means to maintain said inner frame means compressively against said center means; and window means in said inner and outer frame means over which said membrane means is disposed, said window means begin in a plane that is generally perpendicular to the plane of said working electrode such that X-ray beams can be transmitted through said window means and said membrane means onto said working electrode.

11. The electrochemical cell as set forth in claim 10 wherein said center means is formed of a single piece of polymeric plastic material.

12. The electrochemical cell as set forth in claim 10 wherein said counter electrode is made of an inert metal wire and traverses the full length of said working electrode.

13. The electrochemical cell as set forth in claim 10 wherein said reference electrode is disposed in close proximity of said working electrode.

14. The electrochemical cell as set forth in claim 10 wherein said working electrode includes a metal foil to which working electrode leads are coupled at opposite ends of said working electrode.

15. The electrochemical cell as set forth in claim 14 wherein said working electrode leads are mounted in said center means in tight-fitting polymeric plastic tubes so as to insulate said working electrode leads from said electrolyte.

16. The electrochemical cell as set forth in claim 10 including vent means and access tubes extending through said center means into said electrolyte cavity, said vent means and access tubes being made of polymeric plastic tubing that are tightly disposed in holes in said center means.

17. The electrochemical cell as set forth in claim 10 wherein the thickness of said cell between said outer frame means is relatively narrow in order to optimize the thickness to the absorption length of said X-ray beams.

18. An electrochemical cell having an electrolyte cavity adapted to contain an electrolyte with at least a working electrode disposed in said electrolyte cavity and submerged in said electrolyte, said electrochemical cell comprising:

first and second outer frame means having respectively first and second outer slit means;

first and second inner frame means having first and second inner slit means, said first inner slit means being aligned with said first outer slit means and second inner slit means being aligned with said second outer slit means;

a center means having said electrolyte cavity in which said working electrode is mounted such that an interface is formed between said working electrode and said electrolyte;

first and second membrane means;

fastening means maintaining said first and second outer frame means, said first and second inner frame means, said first and second membrane means, and said center means in a layer configuration with said first outer frame means, said first inner frame means and said first membrane means being disposed on one side of said center means and said second outer frame means, said second inner frame means and said second membrane means being disposed on an opposite side of said center means such that said first outer slit means and said first inner slit means provide a first window means in a plane that is generally perpendicular to the plane of said working electrode such that X-ray beams can be transmitted through first window means and said first membrane means onto said working electrode and said second outer slit means and said second inner slit means provide a second window means in a plane that is generally perpendicular to the plane of said working electrode such that X-ray beams from said working electrode can exit through said second membrane means and second window means.

19. The electrochemical cell as set forth in claim 18 wherein said fastening means maintains said first outer frame means, said first inner frame means and said first membrane means compressed against said one side of said center means and maintains said second outer frame means, said second inner frame means and said second membrane means compressed against said other side of said center means so as to provide said electrolyte cavity with a liquid seal.

20. The electrochemical cell as set forth in claim 18 wherein said first membrane means is a first thin polymeric plastic membrane and said second membrane means is a second thin polymeric plastic membrane such that said X-ray beams can pass through said first and second membranes.

* * * * *